(12) United States Patent
Cordani et al.

(10) Patent No.: US 8,673,651 B2
(45) Date of Patent: Mar. 18, 2014

(54) LIQUIDS TEST PROBE

(75) Inventors: Peter Cordani, Palm Beach Gardens, FL (US); Anne Cordani, Palm Beach Gardens, FL (US)

(73) Assignee: GelTech Solutions, Inc., Jupiter, FL (US)

( * ) Notice: Subject to any disclaimer, the term of this patent is extended or adjusted under 35 U.S.C. 154(b) by 1234 days.

(21) Appl. No.: 11/266,690

(22) Filed: Nov. 3, 2005

(65) Prior Publication Data

US 2007/0099300 A1    May 3, 2007

(51) Int. Cl.
*G01N 33/00*    (2006.01)

(52) U.S. Cl.
USPC ........... 436/169; 422/400; 422/401; 422/402; 422/68.1; 422/69

(58) Field of Classification Search
USPC .......... 422/50, 55, 56, 58, 68.1, 99, 102, 104, 422/400, 401, 402, 69; 436/169
See application file for complete search history.

(56) References Cited

U.S. PATENT DOCUMENTS

| | | | | |
|---|---|---|---|---|
| 6,153,147 | A * | 11/2000 | Craig | 422/408 |
| 6,203,757 | B1 * | 3/2001 | Lu et al. | 422/58 |
| 6,248,598 | B1 | 6/2001 | Bogema | |
| 6,372,515 | B1 * | 4/2002 | Casterlin et al. | 436/518 |
| 6,514,769 | B2 * | 2/2003 | Lee | 436/518 |
| 6,557,484 | B1 * | 5/2003 | Engelman | 116/206 |
| 6,818,452 | B2 * | 11/2004 | Wong | 436/169 |
| 2002/0150501 | A1 * | 10/2002 | Robertson et al. | 422/56 |

* cited by examiner

*Primary Examiner* — Sam P Siefke
(74) *Attorney, Agent, or Firm* — McHale & Slavin, P.A.

(57) ABSTRACT

A package for holding and disguising a chromatographic test of food and drink is formed in the shape of a drinking straw or stirrer. The package encloses test patches which are sensitive to particular drugs and produce a color change upon contact with the drug. The package has a view port or slit to observe the condition of the test strip upon contact with food and drink.

11 Claims, 3 Drawing Sheets

LIQUIDS TEST PROBE

FIELD OF THE INVENTION

This invention relates to a test probe containing materials for surreptitious in situ chemical testing of food and drink, prior to ingestion, with an immediate read out of the results of the test.

BACKGROUND OF THE INVENTION

The incidence of unintentional ingestion of certain drugs has increased with the availability of legal and illicit drugs. For example, numerous, "date rape" cases have involved providing the victim with a particular drug, such as "Rohypnol" or flunitrazepam, through social activities, such as eating or drinking. Of longer standing, is the use of a Mickey Finn, chloral hydrate, to render an unsuspecting person unconscious.

It is not unheard of to secretly give certain drugs to those persons, who do not wish to participate or do not consent to partake in voluntary ingestion of legal or illegal drugs, either as a joke or with more malevolent intent. Usually, such secret application is through normally ingested materials. For example, the marijuana laced brownie is a fairly notorious story.

DESCRIPTION OF THE PRIOR ART

There are various small test strips in the prior art that are used by laboratory personnel or others to test for the presence of such compounds as amphetamines, barbiturates, benzodiazepines, cocaine, opiates, methadone, marijuana, methamphetamine, phencyclidine, and tricyclic antidepressants. However, these strips are usually used for testing urine samples to detect drug abuse rather than as a preventive measure. One such device is manufactured by American Bio Medica Corporation as "Rapid Drug Screen"™.

Another assay device is found in U.S. Pat. No. 6,248,598 B1 issued Jun. 19, 2001 to Bogema. This test strip also tests for the presence of drugs, in the body, through a sample of saliva.

These devices have certain reagents incorporated into absorbent test strips. These dry test strips contain the reagent(s) in the solid phase providing convenient packaging, handling and testing. A particular reagent will have a chemical reaction in the presence of a particular drug to activate a particular color which is visually evident, as disclosed by Bogema, above. The absorbent strips are protected by a housing to prevent damage or accidental activation. The test strip is either extended outside the housing or an aperture in the housing is exposed to permit the test liquid to contact the test strip.

When the test strips are introduced into urine or saliva, the bodily fluid is absorbed and, through capillary action, comes into contact with the solid reagent chromatographically sensitive to a particular drug. There may be another compound included with the reagent which is activated by the positive reaction of the reagent to produce a certain color change in the test strip. The presence of a certain color after the exposure is an indication of a "positive" test for the drug. The determination is accomplished in a matter of minutes.

The chemistry involved in these prior art test strips is well known, as shown by the above references. The visual results of such testing may include the presence of a particular color for a negative result and another color for a positive result. Also, the negative test result may involve no color change.

These devices and other similar tests determine the presence or absence of certain drugs in the body by sampling the body fluids. These tests are reactive in that the drugs have already been ingested. In contrast, the testing taught by this invention is pro-active to prevent ingestion of certain drugs.

SUMMARY OF THE INVENTION

What is needed to protect the innocent and prevent inadvertent dosing is a small, simple, un-obtrusive, portable device that can be brought into contact with food and drink to determine whether the food or drink is contaminated with certain drugs. Such a device would quickly provide the user with an indication of the presence or absence of certain drugs.

The devices of this invention are packaged in an unobtrusive shape similar to a drinking straw or stirrer. The user may carry one or more of the packages in a purse or clothing pocket. Such a disguised device could be inserted into a suspicious offering without drawing undue attention. The package also serves as the holder and support for the test strip during use of the device.

The devices of this invention are packaged in an unobtrusive shape similar to a drinking straw or stirrer. The user may carry one or more of the packages in a purse or clothing pocket. Such a disguised device could be inserted into a suspicious offering without drawing undue attention. The package also serves as the holder and support for the test strip during use of the device.

The devices may have a series of discrete testing reagents or areas to test more than one offering for a particular drug or to test for different drugs in one offering.

Accordingly, it is an objective of the instant invention to provide an unobtrusive drug testing apparatus for chromatographically determining the presence or absence of a particular drug in the food or drink about to be ingested.

It is a further objective of the instant invention to provide a drug testing apparatus with an appearance similar to normal utensils used to with food or beverages.

It is yet another objective of the instant invention to teach an elongated testing apparatus having several discrete drug testing areas along its length. The drug testing areas each have a viewing port for visually confirming the results of each test.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

Figure 1:
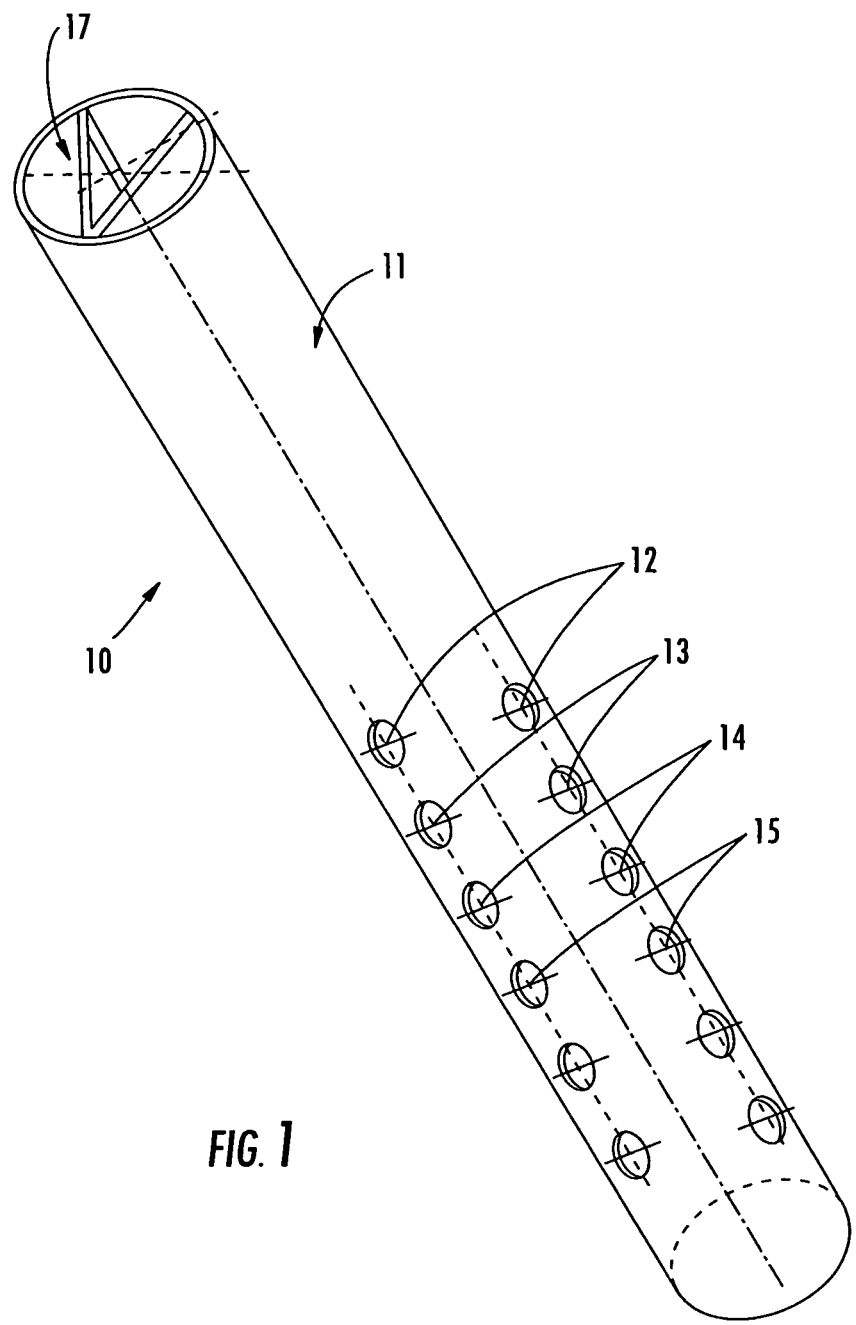
FIG. 1 shows a perspective of the testing strip of this invention.

The disguised package 10, shown in FIG. 1, is approximately the size of a conventional drinking straw or a drink stirrer. It is made of a plastic casing 11 having several pairs of apertures 12, 13, 14, 15 spaced along the length. The test package is normally sterilely wrapped individually to avoid contamination during shipping and storage. Several of the packages may be wrapped together to serially test several samples for the same drug. Alternatively, several of the packages may be wrapped together to test for several different drugs.

The user of the self-defense device would merely bring the uncontaminated test package into contact with the liquid to be tested, for example, by placing the test assembly in a container holding a suspicious drink. Within moments, an indication of the results of the test are visually presented to the user through the apertures.

In FIG. 1, the elongated plastic casing 11 is shown with a tubular shape however, the shape may be rectilinear or multifaceted. The apertures may be uncovered or protected by a transparent or opaque film. The visual results of the test are registered at the apertures. In a preferred embodiment, the tubular casing may be transparent. The pairs of apertures are shown as circular but may be other shapes. The bottom or distal end of the casing may be closed with an end wall or open.

Figure 2:
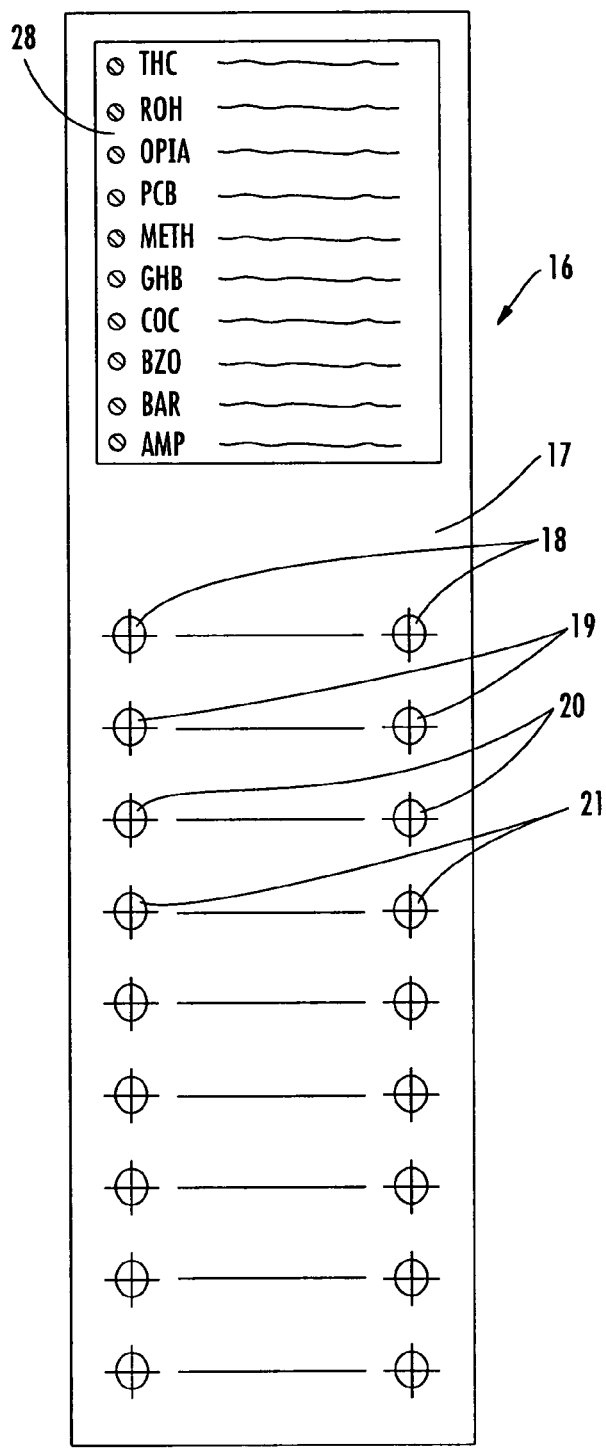
FIG. 2 shows a plan view of the test strip.

As shown in FIG. 2, the test strip 16 has a rectangular base 17 which supports the pairs of solid reagent patches 18, 19, 20, 21. As shown, the pairs of reagent patches are disposed along the opposite margins of the base. The width of the base 17 is greater than the diameter of the casing 11.

As shown in FIG. 1, the base 17 is folded along the longitudinal center line to form a V-shape. The test strip 16 is inserted into the casing 11 and the V-shape expands to secure the test strip in the casing. Additional securement between the base and the casing may be used, in the form of adhesives or heat and pressure. When the base 17 is inserted into the casing 11, the reagent patches 18, 19, 20, 21 are aligned with the apertures 12, 13, 14, 15.

Figure 3:
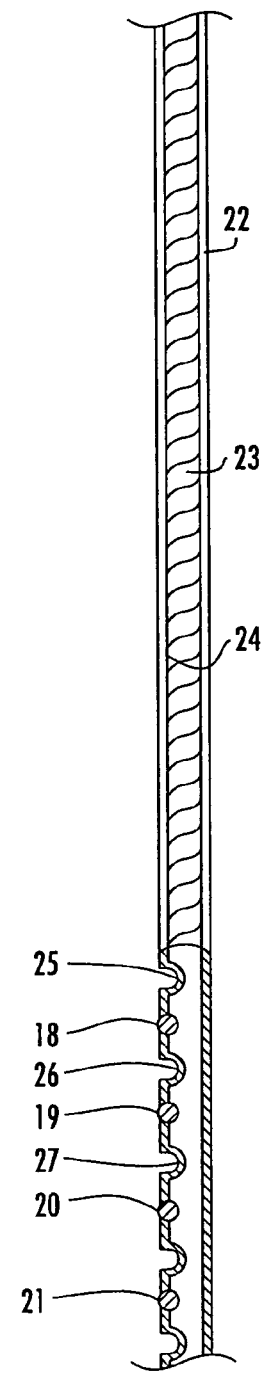
FIG. 3 shows a partial cross section of the test strips.
Figure 4:
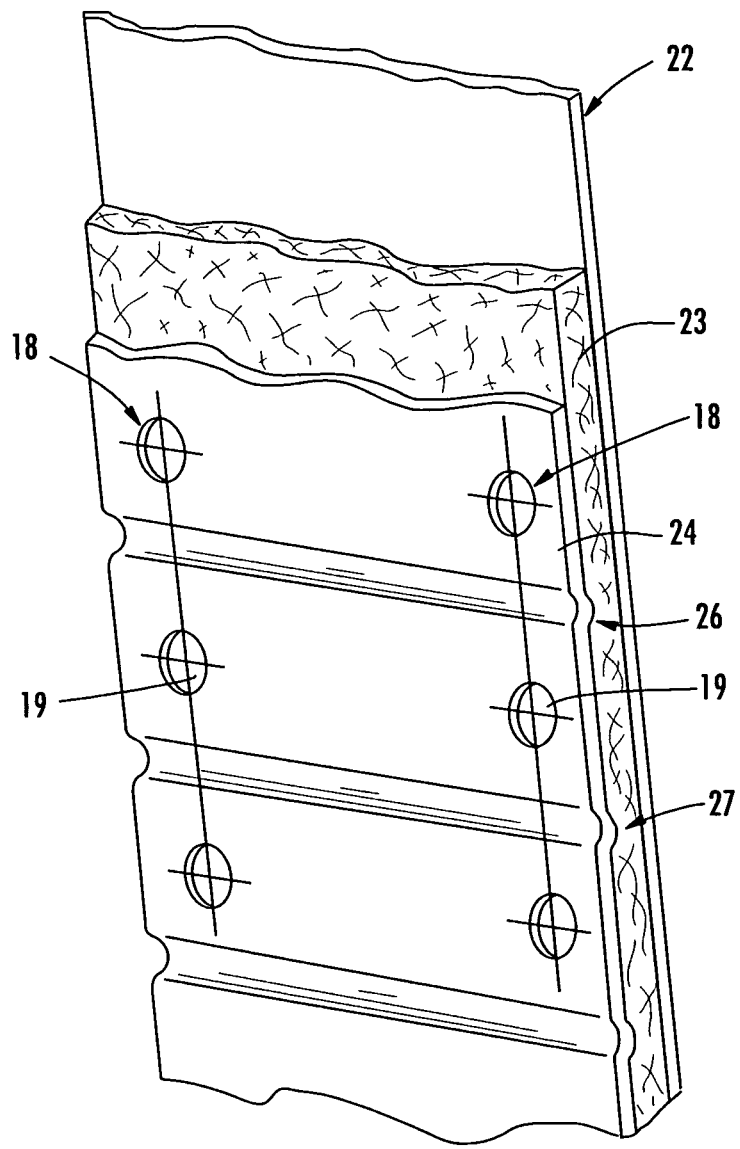
FIG. 4 is a perspective of the test strip.

The base 17 is a multilayered structure, as shown in FIG. 3. As folded in the V-shape, the inner surface of the V-shape is formed of a plastic film substrate 22 of a self sustaining thickness. Laminated to the film 22 is an absorbent fibrous layer 23. The fibers of the fibrous layer may be hydrophobic or hydrophilic. The pairs of reagent patches 18, 19, 20, 21 are fixed to the surface of the fibrous layer and a thin film layer 24 covers the outer layer of the V-shape. The thin film may or may not cover the reagent patches. The outer thin film, the absorbent layer, and the substrate are ultrasonically welded together along transverse welds 25, 26, 27 to form a unitary structure. The transverse welds separate each pair of reagent patches from the other pairs to prevent leakage between patches.

A sample of the test liquid will be absorbed from the container into which the test probe is inserted. The sample will travel from the longitudinal edges of the strip to the reagent patches by capillary action within the fibrous layer or direct contact with the reagent patch. The visual results of the test, if any, will be discernable in a short period of time through the apertures.

The proximal end of the test strip has a comparison table 28 of the location of the reagent patches and the test for a particular drug.

In practice, each pair of reagent patches may include the same reactive chemical compound(s) to test for the same drug or a different reactive chemical compound(s) in each pair of patches to test for different drugs, simultaneously.

By using the disguised package 10, the user has employed self-defense measures to protect herself from potential harm. If the test is negative, the user may consume the tested material, as desired and appropriate. If the test is positive, the user is alerted by the visual indication and may proceed to dispose of the material in any desired manner.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

What is claimed is:

1. A self-defense package for indicating the presence of a particular drug in food or drink before ingestion, said package including an elongated generally tubular casing in the form of a drinking straw or stirrer having a continuous sidewall with open ends, said elongated generally tubular casing enclosing an absorbent fibrous layer elongated strip having an inner surface and outer surface and a distal end and a proximal end, a plurality of test patches fixed to said absorbent layer near said distal end, a plastic film substrate of a self sustaining thickness covers the inner surface of said strip and a thin film covers the outer surface of said strip; said plastic film substrate, said absorbent layer and said thin film being ultrasonically welded together; said test patches each having a separate capillary substrate, said capillary substrate including a particular reagent chromatographically sensitive to a particular drug, whereby said package is unobtrusively manipulated to bring said test module into contact with food or drink wherein liquid from said food or drink will travel from an end of said strip to said reagent patches by capillary action within said fibrous layer and said package presents a visual chromatic indicator as to the presence of a particular drug in the food or drink.

2. A package of claim 1 wherein said continuous sidewall includes an aperture aligned with each said at least one test patch, said strip engaging said sidewall within said enclosure to secure said strip within said enclosure.

3. A package of claim 2 wherein said test patches and said plurality of apertures are aligned with each other for visually inspecting said plurality of test patches.

4. A package of claim 1 wherein said plurality of said test patches are disposed along the length of said strip, said plurality of apertures extending along the length of said enclosure.

5. A package of claim 4 wherein each of said plurality of test patches is chromatographically sensitive to a different drug.

6. A package of claim 2 wherein said strip is folded longitudinally, the longitudinal edges of said strip engaging said sidewall of said enclosure and securing said strip in said enclosure.

7. A package of claim 1 wherein said strip includes a plurality of test patches longitudinally spaced along a margin, a plurality of transverse lines bonding said multilayered strip and separating each of said plurality of test patches.

8. A self defense package for disguising and performing a chromatographic test on food or drink before ingestion, said package comprising an elongated generally tubular casing in the form of a drinking straw or stirrer having a distal end and a hand held proximal end, said elongated generally tubular casing having a continuous side wall having open ends, said distal end having a plurality of spaced apertures adapted to be placed in food or drink, said plurality of apertures being disposed along the length of said distal end of said elongated casing, a multilayered elongated test strip disposed in said casing, said test strip constructed from an absorbent fibrous layer having a plastic film substrate covering an inner surface of said fibrous layer and a thin film covering an outer surface of said fibrous layer; said plastic film substrate, said absorbent layer and said thin film being ultrasonically welded together, said elongated test strip having a plurality of longitudinally spaced test patches chromatographically sensitive to a particular drug, each of said plurality of test patches being aligned with each of said plurality of apertures for viewing test results, each of said plurality of test patches separated by lines of bonding whereby food or drink can be surreptitiously visually tested for the presence of a particular drug by placing said package in contact with food or drink wherein liquid from said food or drink will travel from an end of said strip to said reagent patches by capillary action within said fibrous layer.

9. A package of claim 8 wherein said plurality of test patches each are chromatographically sensitive to a different drug.

10. A package of claim 8 wherein said strip is folded longitudinally in a V-shape with the longitudinal edges of said strip engaging said casing to secure said strip in said casing.

11. A method of self defense comprising the steps of
- (a) providing a package having the appearance of a drinking straw, said package comprising an elongated tubular casing having a continuous side wall, a distal open end and a hand held proximal open end, said distal end having a plurality of spaced apertures adapted to be placed in food or drink, said plurality of apertures being disposed along the length of said distal end of said elongated casing, a multilayered elongated test strip disposed in said casing, said test strip constructed from an absorbent fibrous layer having a plastic film substrate covering an inner surface of said fibrous layer and a thin film covering an outer surface of said fibrous layer; said plastic film substrate, said absorbent layer and said thin film being ultrasonically welded together, said elongated test strip having a plurality of longitudinally spaced test patches chromatographically sensitive to a particular drug, each of said plurality of test patches being aligned with each of said plurality of apertures for viewing test results, each of said plurality of test patches separated by lines of bonding whereby food or drink can be surreptitiously visually tested for the presence of a particular drug by placing said package in contact with food or drink;
- (b) inserting said package in a receptacle containing a liquid to be consumed wherein liquid will travel from an end of said strip to said reagent patches by capillary action within said fibrous layer;
- (c) removing said package from said liquid and manipulating said package for visual inspection of said distal end;
- (d) viewing said test patches through said apertures;
- (e) determining the presence or absence of a particular drug; and
- (f) refusing to consume said liquid containing a particular drug.

* * * * *